United States Patent
Rochin et al.

(10) Patent No.: US 6,531,075 B1
(45) Date of Patent: Mar. 11, 2003

(54) STABILIZATION OF PERFLUOROALKYL ALKYL KETONES

(75) Inventors: Christophe Rochin, Cranbury, NJ (US); Christopher Mark Richardson, Bristol (GB)

(73) Assignee: Rhodia Limited, Avonmouth (GB)

( * ) Notice: Subject to any disclaimer, the term of this patent is extended or adjusted under 35 U.S.C. 154(b) by 0 days.

(21) Appl. No.: 09/214,933

(22) PCT Filed: Jul. 16, 1997

(86) PCT No.: PCT/GB97/01937

§ 371 (c)(1),
(2), (4) Date: Oct. 29, 1999

(87) PCT Pub. No.: WO98/02407

PCT Pub. Date: Jan. 22, 1998

(30) Foreign Application Priority Data

Jul. 17, 1996 (GB) ................................................ 9615016

(51) Int. Cl.[7] ........................ C23G 5/028; C11D 7/50; C11D 7/28; C07C 49/86; C07C 17/42
(52) U.S. Cl. ........................ 252/384; 252/364; 252/380; 252/385; 510/412; 568/304; 570/102; 570/123
(58) Field of Search ................................. 252/364, 380, 252/382, 383, 384, 385; 510/405, 407, 411, 412; 568/304, 305, 306, 307, 419; 570/102, 106, 123

(56) References Cited

U.S. PATENT DOCUMENTS

| | | | | |
|---|---|---|---|---|
| 2,229,625 A | * | 1/1941 | Morey | |
| 2,263,010 A | * | 11/1941 | Rahrs | |
| 2,353,209 A | * | 7/1944 | Williams | |
| 2,353,210 A | * | 7/1944 | Williams | |
| 3,137,732 A | * | 6/1964 | Kuper | |
| 3,256,338 A | | 6/1966 | Robey et al. | |
| 3,341,604 A | | 9/1967 | Quelly | |
| 4,524,031 A | | 6/1985 | Millauer et al. | |
| 4,822,922 A | | 4/1989 | Desmurs et al. | |
| 5,093,532 A | * | 3/1992 | Baasner et al. | 568/407 |
| 5,481,029 A | * | 1/1996 | Braun et al. | 568/394 |
| 5,693,639 A | * | 12/1997 | Empfield et al. | 514/227.5 |
| 5,905,174 A | * | 5/1999 | Kanai et al. | 568/411 |
| 5,998,671 A | * | 12/1999 | Van Der Puy | 568/411 |
| 6,262,312 B1 | * | 7/2001 | Goto | 568/394 |

FOREIGN PATENT DOCUMENTS

DE     2 007 658     8/1971

OTHER PUBLICATIONS

Derwent Abstract of DE 2 007 658 (1971).
Farcasiu et al., "Evaluation of Acidity of Strong Acid Catalysts, II. The Strength of Boron Trifluoride–Water Systems", J. of Catalysis, 134:126–133 (1992).

* cited by examiner

*Primary Examiner*—Joseph D. Anthony
(74) *Attorney, Agent, or Firm*—Finnegan, Henderson, Farabow, Garrett & Dunner, LLP

(57) ABSTRACT

Acids having a pKa of less than about 4 may be used to stabilize certain perfluoroalkyl alkyl ketones, particularly a substantially pure perfluoroalkyl alkyl ketone, a substantially pure aqueous solution of a perfluoroalkyl alkyl ketone or a substantially pure hydrate of a perfluoroalkyl alkyl ketone.

22 Claims, No Drawings

STABILIZATION OF PERFLUOROALKYL ALKYL KETONES

The present invention relates to the stabilization of perfluoroalkyl alkyl ketones.

Many perfluoroalkyl alkyl ketones are useful as intermediates e.g. in the synthesis of pharmaceutical products for which they are required at a high level of purity.

It has been found that, even at such high levels of purity, many perfluoroalkyl alkyl ketones lack stability. They degrade on storage. This is of course unacceptable. When a stored compound is subsequently used as an intermediate the yield of the final product is significantly reduced compared with a compound which has not been degraded due to storage.

It has now surprisingly been found that the addition of even small amounts of strong acid substantially improves the storage stability of certain perfluoroalkyl alkyl ketones.

According to one aspect, the present invention provides use of an acid having a pKa of less than about 4 to stabilize a perfluoroalkyl alkyl ketone of the formula (1)

$$Rf\text{---}CO\text{---}R \qquad (1)$$

wherein Rf is a linear or branched perfluoroalkyl group, R is an optionally substituted linear or branched alkyl group and the sum of the number of carbon atoms in R and the number of carbon atoms in Rf is from 2 to 10, preferably from 2 to 5.

Typically the alkyl group R is substituted with one or more functional groups, for example 1, 2 or 3 functional groups. Typically, the or each functional group is selected from CN, OH, Cl, F, SN, $NH_2$ and $NR_1R_2$ wherein $R_1$ and $R_2$ may be the same or different and represent hydrogen or a hydrocarbon group such as a methyl or ethyl group.

Typically, the or each functional group is not α to the carbonyl, that is, it is not attached to the carbon atom of the group R which bonds directly to the carbonyl.

The alkyl group R typically has more than one hydrogen atom. Preferably, the alkyl group R has at least one, more preferably at least 2, hydrogen atoms α to the carbonyl group, i.e. the carbon atom of the group R which bonds directly to the carbonyl group preferably carries at least one, more preferably at least two, hydrogen atoms.

Typically Rf is $CF_3$ or $CF_3CF_2$.

Compounds of formula (1) in which R is —$CHR_1R_2$ wherein $R_1$ and $R_2$, which may be the same or different, represent H or an alkyl group, are particularly unstable. The stabilization of such compounds according to the invention is therefore particularly preferred.

Preferably, the compound of formula (1) is $CF_3COCH_2CH_3$, $CF_3CF_2COCH_3$, $CF_3CF_2COCH_2CH_3$, $CF_3COCH_2CH_2CH_3$ or $CF_3COCH_3$, particularly preferably $CF_3COCH_3$.

The perfluoroalkyl alkyl ketone of formula (1) may typically be supplied, e.g. to the pharmaceutical industry, in substantially pure form or in the form of its substantially pure hydrate. Certain perfluoroalkyl alkyl ketones of formula (1) have a low boiling point and accordingly may be difficult to handle at room temperature. For example, the boiling point of substantially pure 1,1,1-trifluoroacetone is 21–22° C. It is therefore sometimes more convenient to isolate such perfluoroalkyl alkyl ketones as an aqueous solution. Moreover, depending upon the proposed subsequent processing steps for the ketone in question, it may be appropriate to supply it in the form of an aqueous solution which may be used in subsequent synthesis without removal of the water.

According to a second aspect, the present invention provides a stabilized composition consisting of (a) a substantially pure perfluoroalkyl alkyl ketone of formula (1), a substantially pure aqueous solution of a perfluoroalkyl alkyl ketone of formula (1) or a substantially pure hydrate of a perfluoroalkyl alkyl ketone of formula (1), and (b) a stabilizing amount of an acid having a pKa of less than about 4. Typically, the stabilized composition is suitable for use as an intermediate in the synthesis of a pharmaceutical product.

The present invention also provides the use of a composition as defined above as an intermediate in a synthesis of a pharmaceutical product.

According to a further aspect, the present invention provides a method of stabilizing a substantially pure perfluoroalkyl alkyl ketone of formula (1), a substantially pure aqueous solution of a perfluoroalkyl alkyl ketone of formula (1) or a substantially pure hydrate of a perfluoroalkyl alkyl ketone of formula (1), which method comprises contacting the perfluoroalkyl alkyl ketone, aqueous solution or hydrate with an acid having a pKa of less than about 4, capable of stabilizing the perfluoroalkyl alkyl ketone.

A substantially pure perfluoroalkyl alkyl ketone of formula (1) or a substantially pure hydrate of a perfluoroalkyl alkyl ketone of formula (1) is generally more than 95% pure (by weight), preferably more than 98% pure (by weight). Typically, the maximum amount of any single impurity is about 0.5%, preferably about 0.2%, by weight, based on the total amount of sample.

A substantially pure aqueous solution of a perfluoroalkyl alkyl ketone of formula (1) is typically a water solution in which 95% by weight or more of the solute, preferably 98% by weight or more of the solute, consists of the perfluoroalkyl alkyl ketone. Typically, the maximum amount of any single solute other than the perfluoroalkyl alkyl ketone is about 0.5%, preferably about 0.2%, by weight, based on the total amount of solute.

Although reference is made in the present specification to aqueous solutions of perfluoroalkyl alkyl ketones of formula (1), it is understood that this term is intended to cover equilibrium mixtures with the hydrates of the perfluoroalkyl alkyl ketones of formula (1). In some cases the aqueous solution may be an aqueous solution of substantially pure hydrate. For example, when in an aqueous solution, 1,1,1,-trifluoroacetone exists substantially in the form of its hydrate. For a given perfluoroalkyl alkyl ketone, the amount of ketone and the amount of hydrate will vary depending on factors such as the temperature of the solution, the concentration of the solution etc.

Aqueous solutions can be stabilized at any concentration. Typically, the aqueous solutions have a concentration of from 60% to 20% perfluoroalkyl alkyl ketone (w/w).

An acid having a pKa of less than about 4 is used to stabilize the perfluoroalkyl alkyl ketone of formula (1). It is present in an amount suitable to stabilize the perfluoroalkyl alkyl ketone. The perfluoroalkyl alkyl ketone of formula (1) is stabilized by the acid if it is more stable when contacted with the acid than when it is not contacted with the acid. Preferably, stabilized perfluoroalkyl alkyl ketone degrades by less than 5%, more preferably by less than 2%, after is has been stored for 2 months, preferably 3 months, more preferably 6 months.

Enough acid to give 10 ppm (parts by mol) of hydrogen ions, based on the perfluoroalkyl alkyl ketone of formula (1), may suffice. However, it is preferred to use enough acid to give from 20 to 80 ppm, preferably about 50 ppm (parts by mol) hydrogen ions. If a particularly strong acid, such as HCl or triflic acid (HOTf (HOSO$_2$CF$_3$)), is used, it will dissociate completely and the amount of acid used will be the same as the amount of hydrogen ions generated. However, if a weaker acid is used, a greater amount of the acid can be used to compensate for its lower activity. Correspondingly greater amounts of weaker acid may be used to achieve the hydrogen ion concentrations given above.

The maximum amount of acid which can be added is usually dictated by the use to which the perfluoroalkyl alkyl ketone of formula (1) will be put. As mentioned earlier, the perfluoroalkyl alkyl ketone is often required by pharmaceutical manufacturers at a high level of purity. For this reason, it is preferred to use a maximum of 100 ppm acid (parts by mol) based on the perfluoroalkyl alkyl ketone. However, if a greater amount of acid will not adversely affect the synthetic routes in which the perfluoroalkyl alkyl ketone will be used, it is possible to use more than 100 ppm acid (parts by mol). When a very high amount of acid is present, it is expected that the acid itself will promote degradation of the perfluoroalkyl alkyl ketone. However, any concentration of acid can be used which gives an overall increase in the stability of the perfluoroalkyl alkyl ketone.

Acids suitable for use in the present invention have a pKa of less than about 4 in a substantially pure perfluoroalkyl alkyl ketone of formula (1), in an aqueous solution of a perfluoroalkyl alkyl ketone of formula (1) or in a hydrate of a perfluoroalkyl alkyl ketone of formula (1).

When a substantially pure perfluoroalkyl alkyl ketone of formula (1) is stabilized, suitable acids are those with a pKa in the substantially pure perfluoroalkyl alkyl ketone of less than about 4, preferably less than about 2, more preferably less than about 1. Similarly, when an aqueous solution or a hydrate of a perfluoroalkyl alkyl ketone of formula (1) is stabilized, suitable acids are those with a pKa in the aqueous solution or in the hydrate of less than about 4, preferably less than about 2, more preferably less than about 1.

When a substantially pure perfluoroalkyl alkyl ketone of formula 1) is stabilized, preferred acids are those miscible with, or soluble in, the perfluoroalkyl alkyl ketone. Similarly, when an aqueous solution or a hydrate of a perfluoroalkyl alkyl ketone of formula (1) is stabilized, preferred acids are those miscible with, or soluble in, the aqueous solution or hydrate.

Inorganic acids, organic acids and Lewis acids are all suitable for use according to the present invention. Preferred acids are phosphoric acid, phosphonic acid, phosphinic acid, alkyl sulphonic acids typically having up to six carbon atoms, for example methane sulphonic acid, aryl sulphonic acids typically having up to eight carbon atoms, for example p-toluenesulphonic acid, perfluoroalkyl carboxylic acids typically having up to six carbon atoms, for example trifluoroacetic acid, H$_2$SO$_4$, hydrogen sulphate, HCl, HOTf, acetic acid and BF$_3$. CF$_3$CO$_2$ is particularly suitable when a substantially pure perfluoroalkyl alkyl ketone of formula (1) is stabilized.

Obviously, acids which react with and degrade the perfluoroalkyl alkyl ketone of formula (1) to such an extent as to offset any stabilizing effect are not suitable for use in the present invention.

The acids are typically used in pure or substantially pure form or as an aqueous solution, for example a 20% aqueous solution. They are also typically used as solutions in diethyl ether or ethanol.

The acid and the perfluoroalkyl alkyl ketone of formula (1) may be contacted in any way. Thus, the acid may be added to the perfluoroalkyl alkyl ketone before storage, or the perfluoroalkyl alkyl ketone may be placed into storage containers which already contain the acid.

The following Examples serve to illustrate the invention.

EXAMPLE 1

50 ppm (parts by mol) HCl, based on the 1,1,1-trifluoroacetone, were added to a sample of substantially pure 1,1,1-trifluoroacetone.

The purity of the 1,1,1-trifluoroacetone was determined by $^1$H and $^{19}$F NMR at intervals. The results are shown in Table 1 below.

TABLE 1

| Days | % 1,1,1-trifluoroacetone |
| --- | --- |
| 0 | 99.66 |
| 16 | 99.66 |
| 31 | 99.66 |
| 65 | 99.74 |
| 132 | 99.67 |

EXAMPLE 2

50 ppm (parts by mol) of HCl, based on the 1,1,1-trifluoroacetone, were added to a sample of a substantially pure 70% aqueous solution of 1,1,1-trifluoroacetone. The purity of the 1,1,1-trifluoroacetone was determined by $^1$H and $^{19}$F NMR at various intervals. The results are shown in Table 2 below.

TABLE 2

| Days | % Purity |
| --- | --- |
| 0 | 99.88 |
| 50 | 99.77 |
| 85 | 99.82 |
| 131 | 99.81 |

Comparative Example 1

A 99% pure sample of 1,1,1-trifluoroacetone was stored for two months without any acid addition.

At the end of two months, the 1,1,1-trifluoroacetone content of the sample was found to be only 70%.

What is claimed is:

1. A method for stabilizing a perfluoroalkyl alkyl ketone of formula (1):

$$Rf—CO—R \qquad (1)$$

wherein Rf is a linear or branched perfluoroalkyl group, R is an optionally substituted linear or branched alkyl group and the sum of the number of carbon atoms in R and the number of carbon atoms in Rf is from 2 to 10, which comprises adding to said perfluoralkyl alkyl ketone of the formula 1 an amount of an acid having a pKa of less than about 4 or a Lewis acid, said amount being such as to provide at least 10 ppm of hydrogen ions, per mole of perfluoroalkyl alkyl ketone.

2. A method according to claim 1 wherein the sum of the number of carbon atoms in R and the number of carbon atoms in Rf is from 2 to 5.

3. A method according to claim 1 wherein R is CHR$_1$R$_2$ wherein R$_1$ and R$_2$, which may be the same or different, represent H or an alkyl group.

4. A method according to claim 1 wherein R is substituted with one or more functional groups selected from CN, OH, Cl, F, SH, $NH_2$ and $NR_1R_2$ wherein $R_1$ and $R_2$ may be the same or different and represent hydrogen or a hydrocarbon group.

5. A method according to claim 1 wherein the perfluoroalkyl alkyl ketone is $CF_3COCH_2CH_3$, $CF_3CF_2COCH_3$, $CF_3CF_2COCH_2CH_3$, $CF_3COCH_2CH_2CH_3$ or $CF_3COCH_3$.

6. A method according to claim 1 wherein the acid is phosphoric acid, phosphonic acid, phosphinic acid, an alkyl sulphonic acid, an aryl sulphonic acid, a perfluoroalkyl carboxylic acid, HCl, $H_2SO_4$, hydrogen sulphate, $HOSO_2CF_3$, acetic acid or $BF_3$.

7. A method according to claim 1, wherein the acid has a pKa of less than about 2.

8. A method according to claim 7 wherein the acid has a pKa of less than about 1.

9. A method of stabilizing a substantially pure perfluoroalkyl alkyl ketone of formula (1)

wherein Rf is a linear or branched perfluoroalkyl group, R is an optionally substituted linear or branched alkyl group and the sum of the number of carbon atoms in R and the number of carbon atoms in Rf is from 2 to 10, a substantially pure aqueous solution of a perfluoroalkyl alkyl ketone of formula (1), or a substantially pure hydrate of a perfluoroalkyl alkyl ketone of formula (1), which method comprises adding to the perfluoroalkyl alkyl ketone, aqueous solution or hydrate an acid having a pKa of less than about 4 or a Lewis acid, in an amount to provide at least 10 ppm of hydrogen ions, per mole of perfluoroalkyl alkyl ketone, to stabilize the perfluoroalkyl alkyl ketone.

10. A method according to claim 9 wherein the acid is present in an amount to give from 10 ppm to 100 ppm of hydrogen ions per mole of the perfluoroalkyl alkyl ketone.

11. A method according to claim 9 wherein the acid is present in an amount to give about 50 ppm of hydrogen ions, per mole of perfluoroalkyl alkyl ketone.

12. A method according to claim 9 wherein the acid has a pKa of less than about 2.

13. A method according to claim 9 wherein the acid has a pKa of less than about 1.

14. A method according to claim 9 wherein the acid is phosphoric acid, phosphonic acid, phosphinic acid, an alkyl sulphonic acid, an aryl sulphonic acid, a perfluoroalkyl carboxylic acid, HCl, $H_2SO_4$, hydrogen sulphate, $HOSO_2CF_3$, acetic acid or $BF_3$.

15. A stabilized composition comprising:

(a) a substantially pure perfluoroalkyl alkyl ketone of formula (1)

wherein Rf is a linear or branched perfluoroalkyl group, R is an optionally substituted linear or branched alkyl group and the sum of the number of carbon atoms in R and the number of carbon atoms in Rf is from 2 to 10, a substantially pure aqueous solution of a perfluoroalkyl alkyl ketone of formula (1), or a substantially pure hydrate of a perfluoroalkyl alkyl ketone of formula (1); and (b) a stabilizing amount of an acid having a pKa of less than about 4 or a Lewis acid, in an amount to provide at least 10 ppm of hydrogen ions, per mole of perfluoroalkyl alkyl ketone.

16. A composition according to claim 15 wherein the acid is present in an amount to give from 10 to 100 ppm of hydrogen ions per mole of the perfluoroalkyl alkyl ketone.

17. A composition according to claim 15 wherein the acid has a pKa of less than about 2.

18. A composition according to claim 15 wherein the acid is present in an amount to give about 50 ppm of hydrogen ions, per mole of the perfluoroalkyl alkyl ketone.

19. A composition according to claim 15 wherein the acid has a pKa of less than about 1.

20. A composition according to claim 15 wherein the acid is phosphoric acid, phosphonic acid, phosphinic acid, an alkyl sulphonic acid, an aryl sulphonic acid, a perfluoroalkyl carboxylic acid, HCl, $H_2SO_4$, hydrogen sulphate, $HOSO_2CF_3$, acetic acid or $BF_3$.

21. A method for the synthesis of a pharmaceutical product, which comprises synthesizing the pharmaceutical product using an intermediate which comprises a composition as claimed in claim 15.

22. An intermediate in the synthesis of a pharmaceutical product which comprises a composition as claimed in claim 15.

* * * * *